(12) United States Patent
Munn

(10) Patent No.: US 7,526,331 B2
(45) Date of Patent: Apr. 28, 2009

(54) ENHANCED CARDIAC RADIONUCLIDE IMAGING TECHNIQUES

(76) Inventor: Charles S. Munn, 2555 Grace Dr., Santa Rosa, CA (US) 95404-2606

( * ) Notice: Subject to any disclaimer, the term of this patent is extended or adjusted under 35 U.S.C. 154(b) by 303 days.

(21) Appl. No.: 10/894,390

(22) Filed: Jul. 19, 2004

(65) Prior Publication Data

US 2005/0015008 A1    Jan. 20, 2005

Related U.S. Application Data

(60) Provisional application No. 60/496,352, filed on Aug. 19, 2003, provisional application No. 60/489,738, filed on Jul. 23, 2003, provisional application No. 60/488,541, filed on Jul. 18, 2003.

(51) Int. Cl.
*A61B 6/00* (2006.01)

(52) U.S. Cl. ........................ 600/436; 600/407

(58) Field of Classification Search ............. 600/407, 600/450, 481, 436, 508
See application file for complete search history.

(56) References Cited

U.S. PATENT DOCUMENTS 5,174,987 A * 12/1992 Takaichi et al. ............ 424/9.36
6,231,834 B1   5/2001 Unger et al.
6,884,407 B1 * 4/2005 Unger ...................... 424/9.52

2004/0064039 A1   4/2004 Belardinelli

OTHER PUBLICATIONS

P. Pouderoux, MD. et al., "Effect of Carbonated Water on Gastric Emptying and Intragastric Meal Distribution", Jan. 1997, Digestive Diseases and Sciences, vol. 42, No. 1, pp. 34-39.*
Pedro E. Urena, MD et al., "Ejection fraction by radionuclide ventriculography and contrast left ventriculogram", Jan. 1999, J Am. Coll. Cardiol., vol. 33, pp. 180-185.*
Farooq P. Agha et al., "Comparison of Two Effervescent Agents for Double-contrast Upper Gastrointestinal Tract Radiography", Nov. 1985, Radiology, vol. 157, pp. 533-534.*
Richard L. Wahl et al., "Gastric Air Contrast: Useful Adjunct to Hepatic Artery Scintigraphy", Jan. 1984, AJR, vol. 143, pp. 321-325.*
George M. Segall et al., "Prone Versus Supine Thallium Myocardial SPECT: A Method to Decrease Artificial Inferior Wall Defects", Nov. 1989, The Journal of Nuclear Medicine, vol. 30, pp. 548-555.*

(Continued)

*Primary Examiner*—Eric F Winakur
*Assistant Examiner*—Katherine L Fernandez
(74) *Attorney, Agent, or Firm*—Kriegsman & Kriegsman

(57) ABSTRACT

A cardiac imaging technique comprises (a) introducing a sufficient quantity of a not highly attenuating gas into the stomach of a patient to distend the stomach wall of the patient; and (b) while the stomach wall of the patient is distended, performing radionuclide imaging of the heart and/or of the heart's contents. Preferably, the gas used to distend the stomach wall is introduced into the patient (i) by having the patient ingest a substance that, when contacted with water or with stomach contents, produces the gas, (ii) by having the patient imbibe a liquid which has been mixed or combined with a gas-producing substance, or (iii) by having the patient imbibe a liquid into which the gas has been dissolved.

9 Claims, 1 Drawing Sheet

OTHER PUBLICATIONS

P. 3, 'Reduction of Extracardiac Activity in Myocardial Perfusion Imaging,' Society of Nuclear Medicine Central Chapter in the News, published by Central Chapter of SNM, Inc. (Lombard, IL), Oct. 14, 2002.

Araujo et al., 'Improved Uniformity in Tomographic Myocardial Perfusion Imaging with Attenuation Correction and Enhanced Acquisition and Processing,' J. Nucl. Med., 41:1139-44 (2000).

Boz et al., 'Which Is Better for Inferior Wall Evaluation: A Full or Empty Stomach?' J. Nucl. Med., 37(10):1916-7 (1996).

Bequm et al., 'Positional Related Shifting Inferior Wall Deficits on Myocardial Perfusion Imaging Caused by Fluid in the Gastric Fundus,' Clin. Nucl. Med., 24:893-4 (1999).

Corbett et al., 'Attenuation corrected cardiac perfusion SPECT,' Current Opinion in Cardiology, 15:330-6 (2000).

DePuey et al., 'Optimal Specificity of Thallium-201 SPECT Through Recognition of Imaging Artifacts,' J. Nucl. Med., 30:441-9 (1989).

DePuey et al., 'Using Gated Technetium-99m-Sestamibi SPECT to Characterize Fixed Myocardial Defects as Infarct or Artifact,' J. Nucl. Med. 36: 952-5 (1995).

Desmarais et al., 'Do False Positive Thallium-201 Scans Lead to Unnecessary Catherterization? Outcome of Patients With Perfusion Defects on Quantitative Planar Thallium—201 Scintigraphy,' J. Am. Coll. Cardiol., 21:1058-63 (1993).

Elson et al., 'Is 'diaphragmatic' attenuation a misnomer?' Int'l. J. Card. Imag., 130:161-4 (1997).

Esquerré et al., 'Prone Decubitus: A Solution to Inferior Wall Attenuation in Thallium-201 Myocardial Tomography,' J. Nucl. Med., 30:398-401 (1989).

Gordon et al., 'The Effect of Diaphragmatic Attenuation on $^{201}$Tl Images,' Clin. Nucl. Med., 4:150-1 (1979).

Freedman et al., 'SPECT Attenuation Artifacts in Normal and Overweight Persons: Insights from a Retrospective Comparison of Rb-82 Positron Emission Tomography and Tl-201 SPECT Myocardial Perfusion Imaging,' Clin. Nucl. Med., 25:1019-23 (2000)/

Halvorsen et al., 'Computed Tomography of the Gastroesophageal Junction,' CRC Critical Reviews in Diagnostic Imaging, 21(3):183-228.

Hammerman et al., 'The Gastric Air-Fluid Sign: Aid in CT Assessment of Gastric Wall Thickening,'Gastrointest. Radiol., 14:109-112 (1989).

Hendel et al., 'The value and practice of attenuation correction for myocardial perfusion SPECT imaging: A joint position statement from the American Society of Nuclear Cardiology and the Society of Nuclear Medicine,' J. Nucl. Med., 43:273-80 (2002).

Insko et al., 'Benign and Malignant Lesions of the Stomach: Evaluation of CT Criteria for Differentiation,' Radiology, 228:166-71 (2003).

Jacobson et al., 'Supine versus Upright Anterior Images: Comparison in Tl-201 Myocardial Scintigraphy,' Radiology, 163:691-5 (1987).

Johnstone et al., 'Effect of Patient Positioning on Left Lateral Thallium-201 Myocardial Images,' J. Nucl. Med., 20:183-8 (1979).

Karantanas et al., 'CT Demonstration of Normal Gastric Wall Thickness: The Value of Administering Gas-Producing and Paralytic Agents,'Computerized Medical Imaging and Graphics, 12(6):333-7 (1988).

Kaufman et al., 'The Lateral Decubitus View: An Aid in Evaluating Poorly Defined Pulmonary Densities in Children,' Am. J. Roenigenol., 129:885-8 (1977).

Kiat et al., 'Quantitative Stress-Redistribution Thallium-201 SPECT Using Prone Imaging:Methodologic Development and Validation,' J. Nucl. Med., 33(8):1509-15 (1992).

Komaki, 'Normal or Benign Gastric Wall Thickening Demonstrated by Computed Tomography,' J. Comput. Assist. Tomoqr., 6(6):1103-7 (1982).

Lette et al., 'Normal Qualitative and Quantitative Tc-99m Sestami Myocardial SPECT: Spectrum of Intramyocardial Distribution During Exercise and at Rest,' Clin. Nucl. Med., 19(4): 336-43 (1994).

Miles, 'How does gated SPET alter reporting of myocardial perfusion studies?' Nucl. Med. Commun., 18:915-21 (1997).

Segall et al., 'Prone Versus Supine Thallium Myocardial SPECT: A Method to Decrease Artifactual Inferior Wall Defects,' J. Nucl. Med., 30:548-55 (1989).

Simonds et al., 'The Prone Chest Film,' Radiology, 116:11-17 (1975)

Tsui, 'The AAPM/RSNA Physics Tutorial for Residents: Physics of SPECT,' RadioGraphics, 16:173-83 (1996).

van Dongen et al., 'Minimizing Liver, Bowel, and Gastric Activity in Myocardial Perfusion SPECT,' J. Nucl. Med., 41:1315-7 (2000).

Wahl et al., 'Gastric Air Contrast: Useful Adjunct to Hepatic Artery Scintigraphy,' AJR, 143:321-5 (1984).

Wintergreen Panel Summaries, J. Nucl. Cardiol., 6:93-155 (1999).

\* cited by examiner

ENHANCED CARDIAC RADIONUCLIDE IMAGING TECHNIQUES

CROSS-REFERENCE TO RELATED APPLICATIONS

The present application claims the benefit under 35 U.S.C. 119(e) of U.S. Provisional Patent Application Ser. No. 60/488,541, filed Jul. 18, 2003, U.S. Provisional Patent Application Ser. No. 60/489,738, filed Jul. 23, 2003, and U.S. Provisional Patent Application Ser. No. 60/496,352, filed Aug. 19, 2003, all of which are incorporated herein by reference.

BACKGROUND OF THE INVENTION

The present invention relates generally to cardiac radionuclide imaging techniques and more particularly to new and improved cardiac radionuclide imaging techniques.

In the practice of human or veterinary medicine, radioactive substances are sometimes used to image various body parts and bodily functions. These radioactive substances may be administered to a patient in a variety of ways, e.g., by being injected, inhaled, ingested, instilled or the like. Images created by capturing or visualizing the radioactivity may be mathematically or otherwise processed or analyzed, depending upon the purposes and goals of the particular examination. This medical field is commonly referred to as "radionuclide imaging" or "nuclear medicine."

Currently, radionuclide imaging is performed in a variety of different clinical and research settings. For instance, in the case of a patient who experiences chest pain when exercising, a myocardial scan of the patient's heart may be performed. Such a myocardial scan typically involves administering a radioactive substance into the bloodstream of the patient and then using the radioactivity of said substance to image the myocardium (heart muscle) while the patient is physically or pharmacologically stressed (and possibly at rest, too, for comparison) in an effort to determine whether the myocardium is receiving sufficient blood flow during exercise. If a coronary artery supplying blood to the myocardium is obstructed in some fashion, it will deliver the radioactive substance to the myocardium more poorly than it otherwise would. As a result, an area of the myocardium that has insufficient radioactive substance delivered to it may be visualized as defective with respect to the remainder of the myocardium. Another type of radionuclide imaging of the heart is a radionuclide ventriculogram (or multiple gated acquisition scan) and involves using radionuclide imaging to examine the blood within the lumen of the chambers of the heart.

Accurate interpretation of images depends upon obtaining, processing and creating images of the highest quality. Falsely positive examinations can lead toward unnecessary therapy or additional testing (one or both of which may be dangerous and/or costly) and away from the actual cause of a patient's problem. One way in which falsely positive interpretations of cardiac radionuclide images occur is that a portion of the heart is obscured from an imaging camera by a bodily structure positioned between the camera and the portion of the heart, said bodily structure preventing the radioactivity emanating from the heart from properly reaching the imaging camera. Such an obscuring of radioactivity emitted by the patient is typically referred to as "attenuation" in the field of nuclear medicine.

In cardiac radionuclide imaging, it is important to distinguish a genuine, anatomic or physiologic defect (representing disease) from an artifactual one, such as one caused by attenuation. A common location in the heart of error caused by attenuation is the inferior (and nearby, especially posteriorly) left ventricular myocardium. The diaphragm, a muscle positioned between the abdomen and the chest, has long and widely been regarded as the cause of this artifact because the inferior wall of the heart is adjacent to the diaphragm. Hence, such an artifactual "inferior wall defect" has typically been considered to be attributable to the diaphragm and is often termed simply "diaphragmatic attenuation." Alternatively, a more recent explanation for artifactual inferior wall defects is that fluid in the stomach, and not the diaphragm, is responsible for attenuation. (The stomach is usually just a few millimeters from the heart, on the opposite side of the diaphragm.)

A modest degree of success in decreasing artifactual inferior wall defects has been achieved by altering the positioning of the patient's body for imaging. For example, with planar technique, improved images may be acquired with the patient upright or right lateral decubitus in position. With single photon emission computed tomography (SPECT), better images are seen with the patient prone or "prone decubitus." Also, electronic gating helps to distinguish this artifact from true defect, and mathematical means exist to diminish the visual effect of such artifacts.

In any event, despite the modest gains in decreasing artifactual inferior wall defects achieved in the manner described above, artifactual inferior wall defects remain a serious and important problem in the general clinical practice of radionuclide imaging of the heart.

Another source of artifact in cardiac radionuclide imaging is radioactivity within the left lobe of the liver, the stomach or the bowel. Such radioactivity may be so intense or close to the heart as to obscure the relatively lesser amount within the nearby heart muscle, thereby preventing portions of myocardium from being visible in the images. In addition, computerized and other methods that are intended to "correct" or to lessen mathematically the effect of radiation from one or more of the liver, stomach and bowel may cause the scan's images to contain nearby areas of heart muscle that appear to have less radioactivity than they actually do.

SUMMARY OF THE INVENTION

It is an object of the present invention to provide a novel cardiac radionuclide imaging technique.

It is another object of the present invention to provide a technique as described above that overcomes at least some of the shortcomings described above.

The present invention is based, at least in part, on the discovery that anatomically inferior and nearby wall defects of the heart that occur during radionuclide imaging and that previously had been attributed to attenuation caused by the diaphragm or by fluid in the stomach are, in fact, more properly attributable to attenuation caused by the fundal wall and possibly nearby cardia wall of the stomach.

The present invention is additionally based, at least in part, on the discovery that such attenuation attributable to the fundal wall and possibly nearby cardia wall of the stomach may be diminished by distension of the stomach and that such distension of the stomach may be achieved by inflating the stomach with a gas, such as carbon dioxide, that is not highly attenuating. Such a gas is preferably introduced into the stomach of a patient whose heart is to be imaged by radionuclide imaging (i) by having the patient ingest a substance that, when contacted with water or with stomach contents, produces the gas, (ii) by having the patient imbibe a liquid which has been mixed or combined with said gas-producing substance, or (iii) by having the patient imbibe a liquid containing dissolved gas. For example, the patient may swallow a quantity of sodium bicarbonate crystals, as well as a volume of water (if desired), to yield a quantity of carbon dioxide gas.

Therefore, in accordance with the teachings of the present invention, there is provided a method for imaging at least a portion of the myocardium of a patient, said method comprising the steps of (a) introducing a sufficient quantity of a gas into the stomach of the patient to distend at least the fundal wall of the stomach of the patient, said gas not being highly attenuating for radionuclide imaging; and (b) while at least the fundal wall of the stomach of the patient is distended, performing radionuclide imaging of at least a portion of the myocardium of the patient.

According to another aspect of the present invention, there is provided a method for imaging at least a portion of the contents within one or more chambers of the heart of a patient, said method comprising the steps of (a) introducing a sufficient quantity of a gas into the stomach of the patient to distend at least the fundal wall of the stomach of the patient, said gas not being highly attenuating for radionuclide imaging; and (b) while at least the fundal wall of the stomach of the patient is distended, performing radionuclide imaging of at least a portion of the contents within one or more chambers of the heart of the patient.

Additional objects, as well as features and advantages, of the present invention will be set forth in part in the description which follows, and in part will be obvious from the description or may be learned by practice of the invention. In the description, reference is made to the accompanying drawings which form a part thereof and in which is shown by way of illustration various embodiments for practicing the invention. The embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate various embodiments of the invention and, together with the description, serve to explain the principles of the invention. In the drawings wherein like reference numerals represent like parts.

DETAILED DESCRIPTION OF PREFERRED EMBODIMENTS

Figure 1:
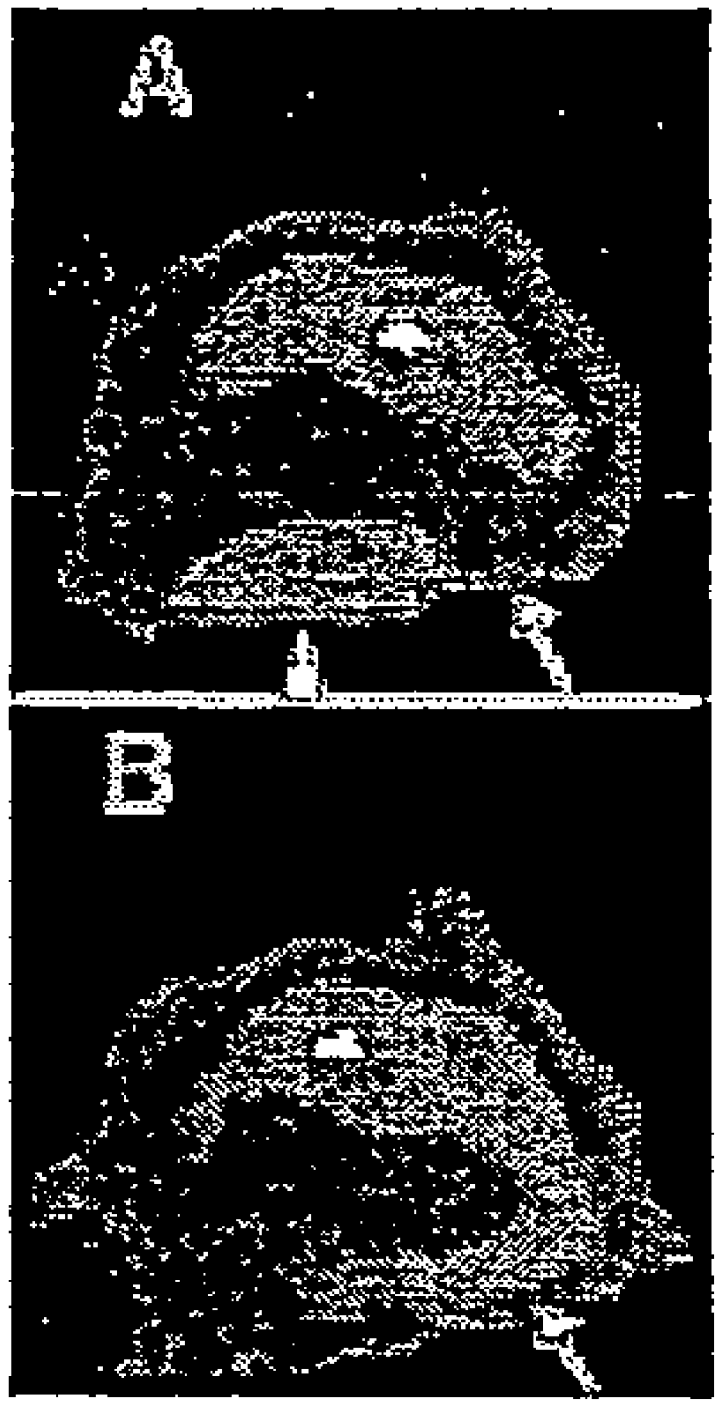
FIG. 1(A) is a vertical long axis 99 mTc sestamibi stress single photon emission computed tomographic (SPECT) myocardial perfusion image prior to gastric distension (with the arrow therein denoting defective perfusion inferoapically and the arrowhead therein denoting a large area of radioactivity due to the left lobe of liver)
FIG. 1(B) is a vertical long axis 99 mTc sestamibi stress single photon emission computed tomographic (SPECT) myocardial perfusion image with gastric distension after oral administration of effervescent granules (with the arrow therein denoting a much improved visualization of inferoapical area; note the absence of liver).

As noted above, the present invention is based, at least in part, on the unexpected findings that artifactual inferior wall defects of the heart that occur during radionuclide imaging are often attributable to attenuation caused by the fundal wall and possibly nearby cardia wall of the stomach and that such attenuation may be diminished by distending the stomach through inflation with a gas that is not highly attenuating.

Although not wishing to be limited to any particular theory behind the invention, the present inventor offers the following explanation as to why the invention achieves its desired effect: The stomach is usually just a few millimeters from the heart, on the other side of the diaphragm. It has recently been proposed that liquid in the stomach might sometimes be responsible for inferior defects. In fact, in one such study (Begum et al., "Positional related shifting inferior wall deficits on myocardial perfusion imaging caused by fluid in the gastric fundus," *Clin. Nucl. Med.*, 24:893-4 (1999), which is incorporated herein by reference), seven of 48 patients experiencing such defects had their defects resolved after being turned prone. That finding is in keeping with other similar studies, but liquid would seem to be an unusual cause for such defects since defects are seen with reasonable frequency in patients who have fasted long enough for their stomachs to be essentially empty and since no evidence is provided in that study of confirmation of the presence of liquid. Perhaps liquid in the fundus is indeed a confounding element in some patients, but it would seem not to be the primary problem.

By contrast, the fundal wall and possibly the nearby cardia wall of the stomach is a more likely cause for attenuation than the recently suspected stomach liquid or the generally and historically inculpated diaphragm. For the stomach wall to be culpable for attenuation, several criteria need to be met: First, the stomach wall thickness needs normally to be sufficiently bulky in some patients to attenuate cardiac radioactivity. Second, that thickness needs to change with position. Third, those positions that cause the portions of stomach wall closest to inferior (or inferoposterior) left ventricle to become thinner need also to cause fewer and milder inferior wall defects.

In confirmation of meeting the above criteria, the present inventor underwent supine CT (computed tomography) scanning of his own fasted stomach (presumed to be normal) before and after ingesting the contents of a 4 g packet of E-Z-GAS® II effervescent granular crystals (E-Z-EM, Inc., Westbury, N.Y.), together with 30 cc water. Such effervescent crystals (primary active ingredient: 2.2 g sodium bicarbonate) are presently in wide use to create carbon dioxide in the stomach for air contrast fluoroscopic examinations. Measurements made of the thickness of the portion of gastric fundal wall nearest to the inferior wall of the left ventricle were 14-16 mm before ingestion of the crystals and 3-4 mm after distension by the crystal suspension. These measurements are in keeping with published normal values, given that stomach volume is generally inversely related to its wall thickness and that underdistension of the stomach has long been known to result frequently in apparent wall thickening.

Additional information relating to gastric wall thickness may be found in a study conducted in Japan in the early 1980s (Komaki, "Normal or benign gastric wall thickening demonstrated by computed tomography," *J. Comput. Assist. Tomogr.*, 6:1103-7 (1982), which is incorporated herein by reference). In the aforementioned study, it was reported that a normal range of 1.2-13 mm (mean=5.0 mm) was determined by CT after ingestion of 200 cc fluid. Of 28 cases in which the stomach was measured as thicker than 13 mm, three proved to have nothing more than focally large gastric rugae; the measurement of only one was reported and that was 23 mm. In addition, some cases were diffusely thick; an example is depicted of stomach wall 19.9 mm thick after ingesting 200 cc fluid, which diminished to 4.1 mm after 3 g of sodium bicarbonate granules and an additional 200 cc of fluid were ingested. The author of this study concluded that thick gastric walls may be observed in normal stomachs and in those with thick gastric rugae.

A few years after the above Japanese study, a Greek study determined a mean, normal, fundus wall thickness of 2.4 mm by CT, with an upper limit of normal of 4 mm (Karantanas et al., "CT demonstration of normal gastric wall thickness: the value of administering gas-producing and paralytic agents," *Comput. Med. Imaging. Graph.*, 12:333-7 (1988), which is incorporated herein by reference). However, the Japanese work was performed with less gastric distension than in the Greek study, in which subjects drank 255 cc of fluid 45 minutes prior to scanning and 55 cc of fluid 10 minutes before imaging, followed by 2 g of a gas-producing agent in approximately 15 cc water. Greater distension may explain the lower mean wall thickness.

In a recent U.S. study of 36 patients (Insko et al., "Benign and malignant lesions of the stomach: evaluation of CT criteria for differentiation," *Radiology*, 228:166-71(2003), which is incorporated herein by reference), the technique included approximately 700 cc of oral fluid 30-45 minutes prior to imaging, plus approximately 450 cc of fluid and 3 g of an effervescent agent in a still additional ~230 cc water immediately prior to imaging. Nineteen patients proved to have gastritis, four to have hiatal hernias and one to be simply normal. Of the 24 cases not warranting further evaluation, three had wall thicknesses greater than 2.0 cm. The four with nothing more than hiatal hernias had a wall thickness range of 0.7-2.0 cm. Thus, even after a prominent volume of fluid was ingested, the stomach wall occasionally remained thick with minimal or even no disease.

Interestingly, stomach wall thickness is dependent not only on the degree of distension, but also upon whether the distension is caused by liquid or gas. In 22% of normal people who had been given approximately 600 cc of fluid to drink 30 minutes prior to CT scanning, an abrupt transition in gastric wall thickness was present at or near the gas-fluid level within the stomach, with the thickness greater than normal at the dependent, fluid-filled portion of stomach and less than 5 mm adjacent to the gas (Hammerman et al., The gastric air-fluid sign: aid in CT assessment of gastric wall thickening, *Gastrointest. Radiol.*, 14:109-12 (1989), which is incorporated herein by reference). Of note, the involved portions of stomach were shown to reverse themselves when a patient was turned prone and scanned again.

In summary, the normal (or benign) stomach wall should indeed be expected in clinical practice occasionally to be focally or diffusely thick even if the stomach is distended, wall thickening should be expected to be greater and more frequent with little or no stomach distension, and the gastric wall should be expected sometimes to be thinner where in contact with gas (in contradistinction to liquid). Stomach wall is mostly muscle; if thick at or near the fundus, it could certainly be an attenuator of nearby, cardiac inferior wall radioactivity.

It is generally known from air contrast fluoroscopic studies that gas rises to the fundus when a patient is prone, upright or in the right lateral position. In those three positions, gravity causes gas to fill the fundus; those precise positions happen also to be those which have been reported to diminish inferior wall defects (Segall et al., "Prone versus supine thallium myocardial SPECT: a method to decrease artifactual inferior wall defects," *J. Nucl. Med.*, 30:548-55 (1989); Jacobson et al., "Supine versus upright anterior images: comparison in TI-201 myocardial scintigraphy," *Radiology*, 163:691-5 (1987); Johnstone et al., "Effect of patient positioning on left lateral thallium-201 myocardial images," *J. Nucl. Med.*, 20:183-8 (1979); Kiat et al., "Quantitative stress-redistribution thallium-201 SPECT using prone imaging: methodologic development and validation," *J. Nucl. Med.*, 33:1509-15 (1992); and Esquerre et al., "Prone decubitus: a solution to inferior wall attenuation in thallium-201 myocardial tomography," *J. Nucl. Med.*, 30:398-401(1989), all of which are incorporated herein by reference). The belief here is that this is causal, not coincidental. When stomach gas is positionally caused to fill the fundus, the gastric wall nearest the inferior wall of the heart may be anticipated to become thinner (in degree and more often), leading generally to fewer and milder defects. In addition to diminishing artifact by thinning the muscular wall of the stomach, air and carbon dioxide are themselves media through which radioactivity travels with particularly little attenuation.

In accordance with the teachings of the present inveniton, gastric fundal gas opens a radionuclide imaging window to the inferior wall of the left ventricle. Interestingly, inferior wall artifactual defects are more common in men than in women (see Elson et al., "Is 'diaphragmatic' attenuation a misnomer? Evaluation of the anatomic cause of 'diaphragmatic' attenuation in SPECT thallium scanning," *Int. J. Card. Imaging*, 13:161-4 (1997); Corbett et al., "Attenuation corrected cardiac perfusion SPECT," *Cur. Opin. Cardiol.*, 15:330-6 (2000); Miles, "How does gated SPET alter reporting of myocardial perfusion studies? *Nucl. Med. Commun.*, 18:915-21(1997); and Freedman et al., "SPECT attenuation artifacts in normal and overweight persons: insights from a retrospective comparison of Rb-82 positron emission tomography and TI-201 SPECT myocardial perfusion imaging," *Clin. Nucl. Med.*, 25:1019-23 (2000), all of which are incorporated herein by reference), and, of fifty consecutive adults measured, the stomach walls of men far more often than women exceeded average.

The precepts of the present invention were observed by the present inventor to be confirmed as follows: Nine patients with promptly noted inferior wall defects were immediately given a single 4 g packet of E-Z-GAS® II effervescent granular crystals (E-Z-EM, Inc., Westbury, N.Y.), together with approximately 30 cc water to swallow and imaging was again performed immediately thereafter. About a third of the patients demonstrated no significant change, a second third of the patients exhibited moderate improvement, and the final third of the patients demonstrated marked improvement (see FIGS. 1(A) and 1(B)). There was no worsening of image quality in any case nor was there any untoward reaction.

This convenient solution to the problem of inferior wall defects may be complementary to positional maneuvers, and the proposed unifying explanation for them all is based on gravity and anatomy.

Finally, in some cases, there may be a further benefit of this technique in regard to additional sources of artifact in myocardial and other scanning, also based on normal anatomy. As noted above, radioactivity within the left lobe of the liver, the stomach and the bowel may be sufficiently intense or close to the heart as to obscure nearby myocardium by scatter; these sources of radioactivity can also present difficulty with regard to radionuclide left ventriculograms and other studies. Also, computerized and other methods of "correction" to lessen mathematically the effect of liver or gut activity may cause nearby areas of myocardium to appear to have less radioactivity than they actually have ("overcorrection").

Gaseous distension of the stomach may in some patients displace left lobe of liver (or bowel) anteriorly, inferiorly or to the right (see es., Wahl et al., "Gastric air contrast: useful adjunct to hepatic artery scintigraphy, *AJR*, 143:321-5

(1984), which is incorporated herein by reference), interposing a bit of gas-filled stomach between diaphragm (thin and adjacent to heart) and left lobe of liver or bowel, which may lessen artifact. Similarly, interposition of air-filled lung between heart and stomach is here offered as an explanation for the diminished defect found with intermittent, inspiratory imaging. Interposition of air-filled lung may also be a supplementary reason why prone and right lateral decubitus positioning yield less defect, since both positions cause better left lung base expansion, and some of that expanded lung may occupy an increased distance between heart and left hemidiaphragm.

The ingestion of water or of water plus milk have both been shown to help to minimize the artifactual effect of abdominal radioactivity activity. Positional change and gaseous gastric distension in accordance with the teachings of the present invention may help to minimize abdominal activity additionally or better than the ingestion of water or water plus milk because air and carbon dioxide are weaker attenuators than water and milk, because luminal radioactivity is moved farther from the heart and gas toward it, and because gas seems to cause the stomach wall to thin better than liquid does in some patients and any contribution to artifact from radioactivity within the wall may be expected to decrease with thinning.

To achieve the necessary gastric distension of the stomach for purposes of the present invention, one may have the patient (i) ingest a substance that, when contacted with water or with stomach contents, produces a gas (like carbon dioxide) that is not highly attenuating, (ii) imbibe a liquid which has been mixed or combined with said gas-producing substance, or (iii) imbibe a liquid containing dissolved gas. An example of a substance which, when contacted with water or with stomach contents, produces a suitable gas is sodium bicarbonate.

The embodiments of the present invention recited herein are intended to be merely exemplary and those skilled in the art will be able to make numerous variations and modifications to it without departing from the spirit of the present invention. All such variations and modifications are intended to be within the scope of the present invention as defined by the claims appended hereto.

What is claimed is:

1. A method for imaging at least a portion of the myocardium of a patient in such a way as to diminish an artifactual inferior wall defect, said method comprising the steps of:

(a) transorally introducing a sufficient quantity of a gas into the stomach of the patient to thin at least the fundal wall of the stomach of the patient, said gas not being highly attenuating for radionuclide imaging, wherein said gas comprises carbon dioxide; and (b) while at least the fundal wall of the stomach of the patient is thinned, performing radionuclide imaging of at least a portion of the myocardium of the patient, wherein said radionuclide imaging comprises myocardial single photon emission computed tomographic (SPECT) imaging.

2. The method as claimed in claim 1 wherein said gas is introduced into the stomach of the patient by having the patient ingest a substance that, when contacted with water or with stomach contents, produces said gas.

3. The method as claimed in claim 2 wherein said substance is sodium bicarbonate.

4. The method as claimed in claim 1 wherein said gas is introduced into the stomach of the patient by having the patient imbibe a liquid which has been mixed or combined with a substance wherein said substance, when contacted with said liquid, produces said gas.

5. The method as claimed in claim 4 wherein said substance is sodium bicarbonate.

6. The method as claimed in claim 1 wherein said gas is introduced into the stomach of the patient by having the patient imbibe a liquid into which said gas has been dissolved.

7. The method as claimed in claim 1 wherein the radionuclide imaging performed is a myocardial scan performed while the patient is physically and/or pharmacologically stressed.

8. The method as claimed in claim 1 wherein said gas is introduced into the stomach of the patient by having the patient ingest about 2 grams of sodium bicarbonate with about 30 cc of water.

9. The method as claimed in claim 1 wherein said radionuclide imaging is performed while the patient is positioned in one of an upright position and a right lateral position.

* * * * *